(12) United States Patent
Zivitz et al.

(10) Patent No.: US 6,485,471 B1
(45) Date of Patent: Nov. 26, 2002

(54) BELLOWED FLUID DELIVERY APPARATUS

(75) Inventors: Maury Zivitz, Indianapolis, IN (US); Raghbir Singh Bhullar, Indianapolis, IN (US); Brian S. Hill, Indianapolis, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/518,817

(22) Filed: Mar. 3, 2000

(51) Int. Cl.[7] .............................................. A61M 5/178
(52) U.S. Cl. ...................... 604/212; 604/216; 604/187; 604/181; 604/200
(58) Field of Search ................................ 604/153, 216, 604/28, 500, 131, 232, 212, 208; 73/1.16, 1.19, 1.05, 1.23

(56) References Cited

U.S. PATENT DOCUMENTS

| | | | |
|---|---|---|---|
| 3,965,897 A | * 6/1976 | Lundquist | 128/220 |
| 4,073,288 A | 2/1978 | Chapman | 128/2 F |
| 4,079,251 A | 3/1978 | Osann, Jr. | 250/231 SE |
| 4,194,386 A | * 3/1980 | Waters | 73/3 |
| 4,406,158 A | * 9/1983 | Allington | 73/61.1 C |
| 4,411,656 A | 10/1983 | Cornett, III | 604/212 |
| 4,560,979 A | * 12/1985 | Rosskopf | 604/131 |
| 4,668,220 A | * 5/1987 | Hayrylenko | 604/155 |
| 5,017,059 A | 5/1991 | Davis | 409/131 |
| 5,147,311 A | * 9/1992 | Pickhard | 604/153 |
| 5,187,479 A | 2/1993 | Johnson, III et al. | 341/6 |
| 5,201,654 A | * 4/1993 | Kuehn et al. | 433/25 |
| 5,267,974 A | * 12/1993 | Lambert | 604/212 |
| 5,584,667 A | 12/1996 | Davis | 417/53 |
| 5,695,464 A | 12/1997 | Viallet | 604/67 |
| 5,696,704 A | * 12/1997 | Semrau | 364/561 |
| 5,817,066 A | * 10/1998 | Goforth | 604/212 |
| 6,077,252 A | * 6/2000 | Siegel | 604/214 |
| 6,109,150 A | * 8/2000 | Saccomanno, III | 81/478 |
| 6,248,093 B1 | * 6/2001 | Moberg | 604/131 |

* cited by examiner

Primary Examiner—Ira S. Lazarus
Assistant Examiner—Tu C. Nguyen
(74) Attorney, Agent, or Firm—Jill L. Woodburn

(57) ABSTRACT

A fluid-delivery apparatus for delivering a medicament to a patient is provided in accordance with the present invention. The apparatus includes a housing defining a passageway, a bellowed ampoule positioned to lie in the passageway of the housing, and a piston. The bellowed ampoule includes a body with first and second ends and is formed to define a cavity configured to contain the medicament. The piston presses the second end of the ampoule toward the first end to dispense the medicament from the cavity. In addition, the fluid-delivery apparatus includes a visible non-linear scale that represents the relationship between a volume of medicament delivered from the first end of the ampoule and a distance that the piston has traveled in the housing toward the first end.

25 Claims, 11 Drawing Sheets

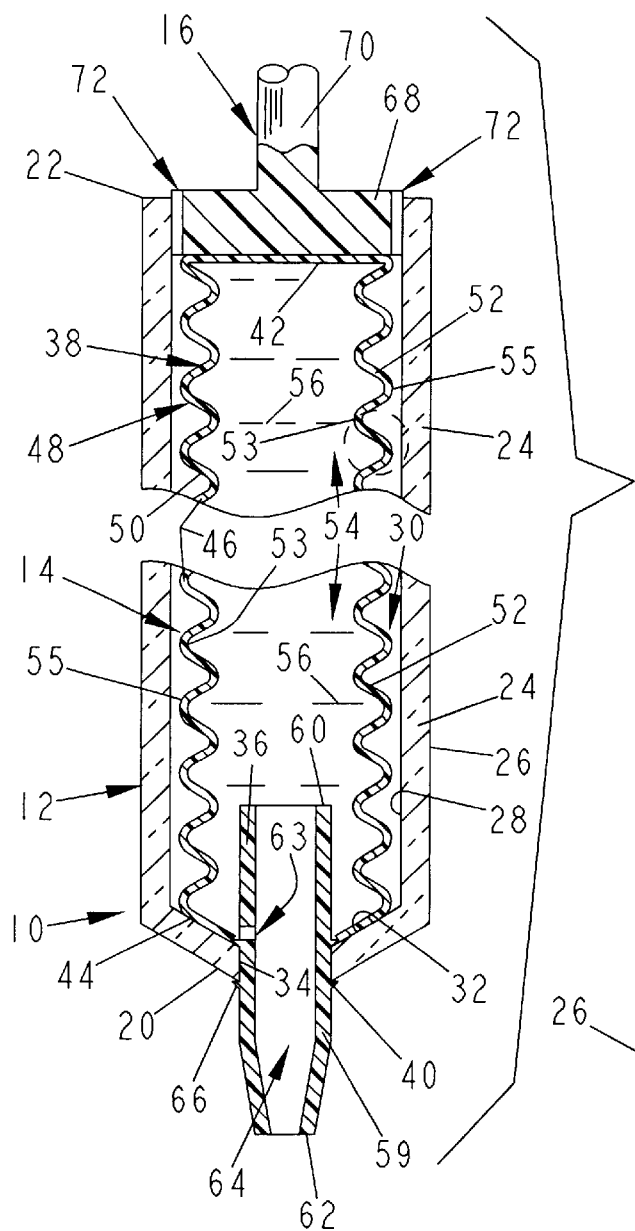
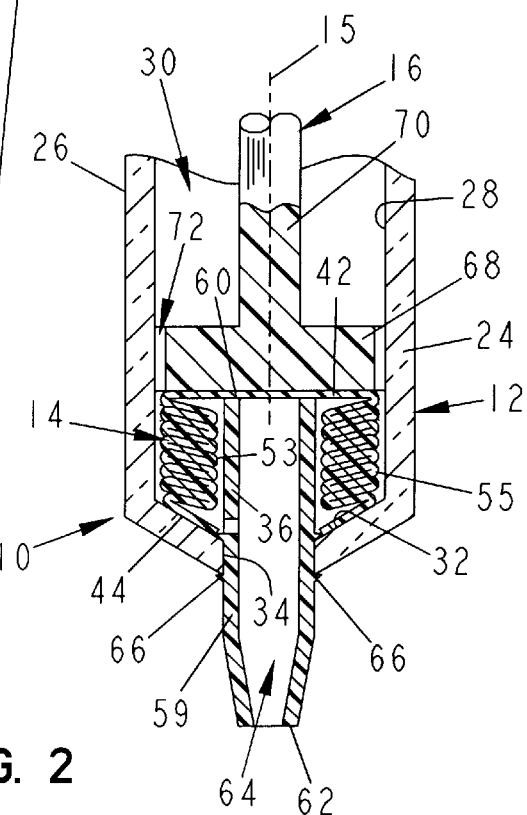
FIG. 1
FIG. 2

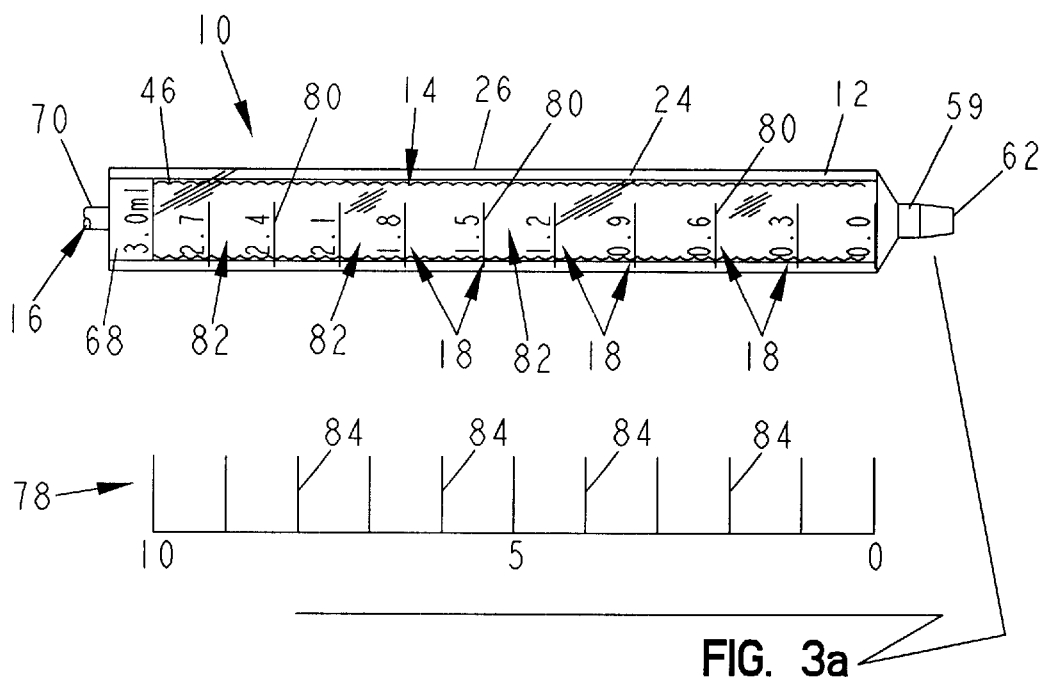
FIG. 3a
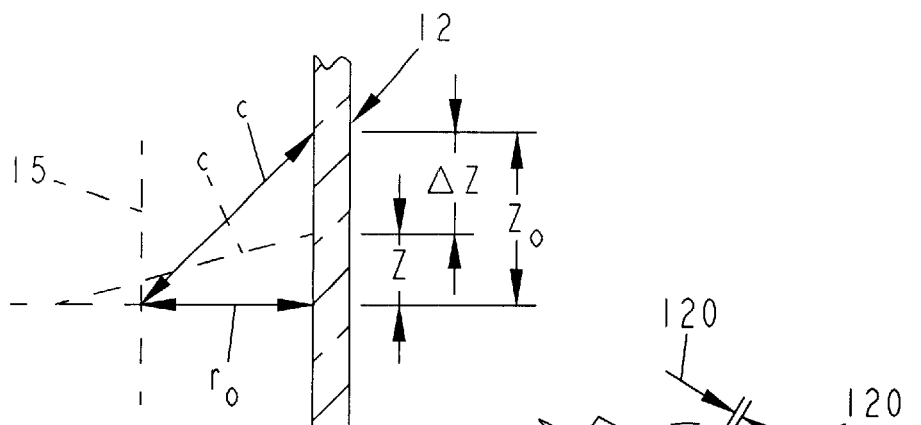
FIG. 3b
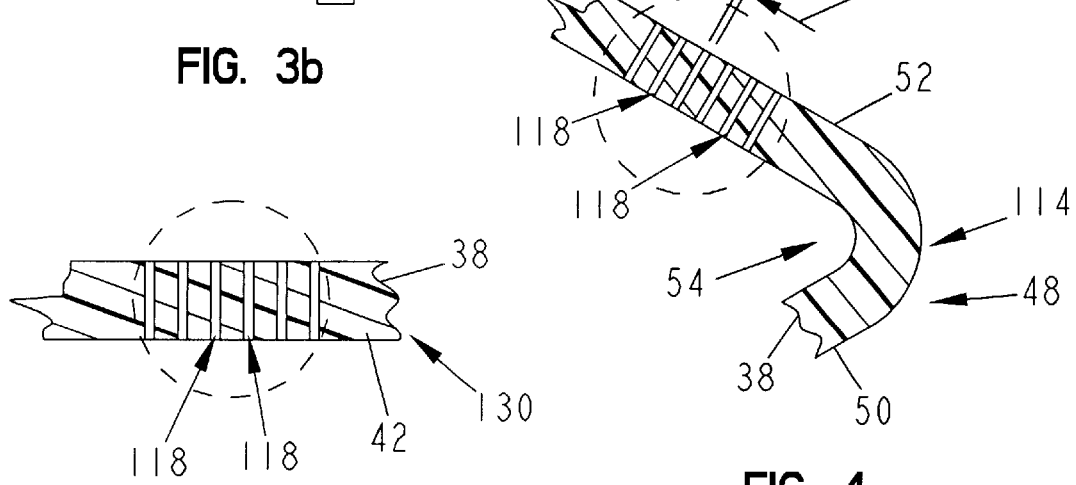
FIG. 5
FIG. 4

US 6,485,471 B1

BELLOWED FLUID DELIVERY APPARATUS

FIELD OF THE INVENTION

This invention relates to a fluid delivery apparatus, and more particularly, to a fluid-delivery apparatus with a bellowed ampoule.

BACKGROUND AND SUMMARY OF THE INVENTION

Syringes that utilize expandable encasements are known. See for example, U.S. Pat. No. 4,073,288 to Chapman and U.S. Pat. No. 5,147,311 to Pickhard. Such traditional syringes, however, do not compensate for the effect of encroachment on the bulk fluid volume within the syringe due to movement of the encasement walls.

According to the present invention a fluid-delivery apparatus for delivering a medicament to a patient is provided, which accounts for the effect of encroachment that occurs as the fluid is-delivered therefrom. This apparatus comprises a housing defining a passageway, a bellowed ampoule positioned to lie in the passageway of the housing, the bellowed ampoule including a body having first and second ends and formed to define a cavity configured to contain the medicament, and a piston. The piston is positioned in the housing and formed to press the second end of the ampoule toward the first end. In addition, the apparatus further comprises a visible non-linear scale representing the relationship between a volume of medicament delivered from the first end of the ampoule and a distance that the piston has traveled in the housing toward the first end.

In accordance with another embodiment of the present invention a fluid-delivery apparatus for delivering a uniform volume of medicament to a patient is provided. The apparatus comprises a housing defining a passageway, a bellowed ampoule positioned to lie in the passageway of the housing, a piston, and a piston-drive system. The bellowed ampoule includes first and second ends and defines a cavity configured to contain the medicament. The piston is formed for movement in the housing to press the second end of the ampoule toward the first end. Further, the piston-drive system adjusts the movement of the piston in the housing so that the medicament is delivered in uniform increments from the first end of the ampoule.

Still further in accordance with another embodiment of the present invention, a method for determining the amount of fluid delivered from a bellowed ampoule positioned in a cylindrical housing having a radius of $r_0$ that is substantially equal to an outermost radius of the ampoule is provided. The method comprises the steps of calculating the relative encroachment function Err of the bellowed ampoule from the equation $$\text{Err} = \Psi \cdot (1 - \Psi/3), \text{ where } \Psi \equiv (c/r_0)\sqrt{1-(z/c)^2},$$

z is the height of one half-fold of one bellow of the ampoule, and c is length of an upper panel of one bellow, depressing the ampoule a pre-determined distance in the housing changing the height z of one half-fold of one bellow, and determining the cumulative volume dispensed $V_d$ from the bellowed ampoule. The cumulative volume dispensed is determined from the equation $$V_d = V_0 - (\pi r_0^2 n z) \cdot [1 - \text{Err}],$$

where $V_0$ is the initial volume of the filled reservoir and n is the number of half folds in the bellowed ampoule.

In addition, in accordance with the present invention a method for delivering a constant linear volume of fluid from a bellowed ampoule positioned in a cylindrical housing having a radius of $r_0$ that is substantially equal to an outermost radius of the ampoule is provided. The method comprises the steps of calculating the relative encroachment function Err of the bellowed ampoule from the equation $$\text{Err} = \Psi \cdot (1 - \Psi/3), \text{ where } \Psi \equiv (c/r_0)\sqrt{1-(z/c)^2},$$

z is the height of one half-fold of one bellow of the ampoule, and c is length of an upper panel of one bellow, determining the cumulative volume dispensed $V_d$ from the bellowed ampoule from the equation $$V_d = V_0 - (\pi r_0^2 n z) \cdot [1 - \text{Err}],$$

where $V_0$ is the initial volume of the filled reservoir and n is the number of half folds in the bellowed ampoule, and compressing the ampoule in the housing at a rate sufficient to achieve a constant linear flow of fluid from the ampoule in accordance with the equation $$dz/dV_d = \left(-\pi n \cdot \left[r_0^2 \cdot [1 - \text{Err}] + \left(\frac{1 + 2\psi/3}{\psi}\right) \cdot z^2\right]\right)^{-1}.$$

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 1 is a cross-sectional view of a fluid-delivery apparatus in accordance with the present invention, showing the apparatus including a housing, a bellowed ampoule positioned in the housing, and a piston;

FIG. 2 is a view similar to FIG. 1 following movement of the piston toward a first end of the bellowed ampoule;

FIG. 3a is a plan view of the apparatus of FIG. 1 illustrating monotonic indicia positioned that represents the relationship between a volume of medicament delivered from the bellowed ampoule and a distance that the piston has traveled in the housing;

FIG. 3b is an enlarged diagrammatic view illustrating the relative dimensions of one half-fold of the bellowed ampoule relative to the housing;

FIG. 4 is an enlarged view of another embodiment of a bellowed ampoule of the present invention;

FIG. 5 is an enlarged view of another embodiment of the bellowed ampoule of the present invention;

DETAILED DESCRIPTION OF THE DRAWINGS

Figure 6:
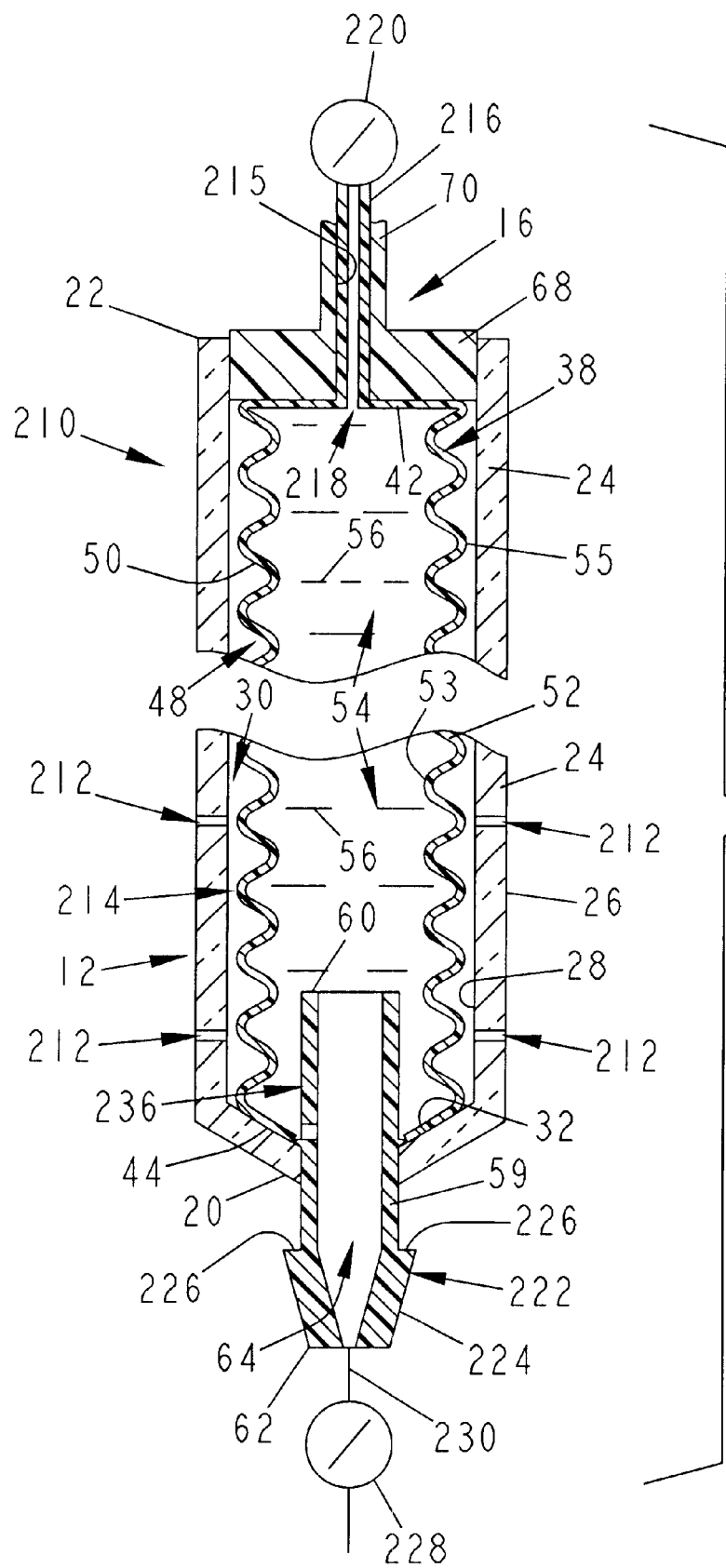
FIG. 6 is a cross-sectional view of another embodiment of the present invention.

A fluid-delivery apparatus 10 is provided in accordance with the present invention enabling a user to deliver fluids precisely. Apparatus 10 is formed for use in a manual mode of operation. As shown in FIGS. 1–3, apparatus 10 includes a housing 12, a bellowed ampoule 14 positioned in housing 12, a piston 16 engaging ampoule 14, and a monotonic scale 18. Scale 18 represents the relationship between a volume of medicament delivered from ampoule 14 and a distance that piston 16 has traveled in housing 12 to enable the user to deliver an accurate dose of medicament from ampoule 14. Various aspects of the invention are presented in FIGS. 1–9 and 12–13, which are not drawn to scale and wherein like components in the several views are numbered alike.

Housing 12 holds ampoule 14 therein and provides a support for scale 18. As shown in FIG. 1, housing 12 is a smooth-bore, tight fitting cylindrical tube that prevents bulging of ampoule 14 under pressure. Housing 12 includes opposite ends 20, 22 and a cylindrical wall 24 extending between opposite ends 20, 22. Wall 24 includes an exterior surface 26 and an interior surface 28 that defines a passageway 30 extending between opposite ends 20, 22. A ramped seat 32 extends into passageway 30 adjacent to end 20 and defines an opening 34 into passageway 30. Housing 12 is preferably constructed of a transparent plastic material. It is appreciated, however, that housing 12 may be formed in a wide variety of shapes and sizes and be constructed of a wide variety of commercially available glass, metals, ceramics, and plastics such as high density polyethylene, acrylonitrile butadiene styrene (ABS), polypropylene, or the like in accordance with the disclosure.

Ampoule 14 is positioned in passageway 30 adjacent to interior surface 28 and is formed to dispense a predetermined volume of medicament 56 from housing 12. Ampoule 14 includes a body 38 and a travel limit 36 coupled to body 38. Body 38 has a first open end 44 situated on seat 32, a second closed end 42 adjacent to piston 16, and a wall 46 extending between ends 42, 44. Wall 46 includes bellows 48 having a lower panel 50 generally facing end 44, an upper panel 52 generally facing end 42, and interior and exterior corners 53, 55 positioned between lower and upper panels 50, 52. Referring now to FIG. 2, lower and upper panels 50, 52 fold upon one another about travel limit 36 as end 42 of ampoule 14 moves in passageway 30 toward end 44. In addition, wall 46 cooperates with ends 42, 44 to define a cavity 54 that is sized to receive medicament 56, such as insulin. It is appreciated, however, that a wide variety of fluids may be dispensed from apparatus 10 in accordance with this disclosure.

Ampoule 14 is constructed of a thermoplastic polymeric material, for example ABS, acetal, acrylic, polycarbonate, polyester, polyethylene, fluroplastic, polyimide, nylon, polyphenylene oxide, polypropylene, polystyrene, polysulphone, polyvinyl chloride, poly (methacrylate), poly (methyl methacrylate), or mixture or copolymers thereof. Ampoule 14 is constructed using multi-resin injection molding. Such a molding process is commercially available from H. Weidmann A G, Neue Jonastrasse 60, CH-8640 Rapperswil, Switzerland. Multi-resin injection molding enables body 38 and travel limit 36 to be created as one unit. Multi-resin injection molding requires that a suitable multi-resinous material be selected to impart desired characteristics to ampoule 14 to enable portions of ampoule to have an individualized stiffness and chemically inactive relative to the medicament. Although ampoule 14 is preferably manufactured using multi-resin injection molding, it is contemplated that ampoule 14 may be formed in other well know commercially available methods in accordance with this disclosure and travel limit 36 may be constructed of a metal. In addition, if apparatus 10 is formed for multi-use, panels 50, 52 of body 38 may be reinforced with polycarbonate rings.

Successive, equal compressions of ampoule 14 along axis 15 effuse reduced increments of medicament 56. Medicament 56 is dispensed from ampoule 14 through travel limit 36. As shown in FIG. 1, travel limit 36 is formed as a sleeve 59 that includes an upper surface 60, a lower surface 62, an aperture 63, and a channel 64 extending between upper and lower surfaces 60, 62. It is appreciated that the length and width of sleeve 59 may vary as well as the number of apertures 63 in accordance with this disclosure. In addition, sleeve 59 includes retaining tabs 66 that are flexible and have a tapered portion 40 that extends in a radial direction away from channel 64. Sleeve 59 and tabs 66 cooperate with end 20 to couple ampoule 14 in passageway 30 of housing 12. A syringe or infusion line with a luer lock (not shown) may be coupled to sleeve 59 or formed as one unit with sleeve 59 to further direct the flow of medicament 56. It is appreciated that any number of tubes, reservoirs, or the like may be coupled to sleeve 59 to direct the flow of medicament 56.

As shown in FIG. 2, piston 16 is sized to travel in passageway 30 toward travel limit 36 to press ampoule 14 toward end 44 and dispense medicament 56. Upper surface 60 of travel limit 36 regulates the distance that piston 16 travels in passageway 30. Piston 16 includes a base 68 formed for engagement with closed end 42 of body 38 and a rod 70 extending from base 68 and through end 22 of housing 12.

Base 68 is generally disc-shaped and has a diameter that is substantially equal to the diameter of passageway 30. In addition, base 68 is formed to include apertures 72 that are sized to vent air out from passageway 30 as piston 16 is depressed toward end 20. It is appreciated that base 68 may be formed in a variety of shapes and sizes to cooperate with the shape and size of the housing and may include greater or fewer than two apertures positioned in various locations. Piston 16 preferably is constructed of commercially available metals, ceramics, and plastics such as high-density polyethylene, ABS, polypropylene, or the like in accordance with the disclosure. It is appreciated, however, that piston 16 may be formed in a wide variety of shapes and sizes to correspond with housing 12, or may be formed as one unit with ampoule 14 with multi-resin injection molding.

As shown in FIG. 3, scale 18 is formed on housing 12 to represent the relationship between a volume of medicament 56 delivered from ampoule 14 and a distance that piston 16 has traveled in housing 12. Scale 18 enables the user to deliver an accurate dose of medicament 56 from ampoule 14. Scale 18 includes a series of indicia 80 that are monotonic in spacing. The amount of spacing 82 between indicia 80 is proportional to the volume of cavity 54 that is encroached by bellows 48 as ampoule 14 is compressed. In addition, FIG. 3 shows scale 18 positioned adjacent to a scale 78 wherein indicia 84 have a linear relationship. Indicia 80 are spaced differently from indicia 84 to account for the reduction in volume of cavity 54 of ampoule 14 verses the volume of passageway 30 of housing 12. The source of lost volume relative to a smooth-bore cylinder such as housing 12 having a substantially equivalent radius, is the movement of panels 50, 52 of bellows 48 in the bulk volume of housing 12, as piston 16 is compressed along axis 15.

For the geometry of ampoule 14 as illustrated in FIG. 1, the nonlinearity of volume delivery of medicament 56 versus stroke displacement of piston 16 is calculated as discussed below. The source of lost volume of ampoule 14, relative to housing 12, is the movement of panels 50, 52 of bellows 48 in passageway 30 of housing 12, as piston 16 presses ampoule 14 along axis 15. To extract this encroachment function Err in a relative form, it is only necessary to consider the reduced geometry of one "half-fold" of bellows 48. As shown in FIG. 3b, housing 12 has a radius $r_0$, the initial height of a fold is $z_0$, and a hypotenuse c corresponds to one panel of bellows 48, has a constant length, and moves as piston 16 is compressed to reduce the half-fold height from an initial value of $z_0$ to a reduced height z.

Relative encroachment Err is defined as the encroached volume V (z) of bellowed ampoule 14 divided by the full volume of a cylinder with radius $r_0$ and height z. As the half-fold height z of ampoule 14 decreases, the function Err smoothly increases. Indeed as the half-fold height z decreases from its initial maximum height $z_0$ to z=0, Err increases approximately by the amount $\sqrt{2}$. This relative encroachment Err or the error generated by one half of bellows 48 is given by the expression:

$$Err = \Psi \cdot (1 - \Psi/3), \quad (1)$$

where $$\Psi \equiv (c/r_0)\sqrt{1-(z/c)^2}. \quad (2)$$

The cumulative volume dispensed from bellowed ampoule 14 is given by the equation:

$$V_d = V_0 - (\pi r_0^2 nz) \cdot [1 - Err(z)], \quad (3)$$

where $V_d$ is the volume of medicament delivered from the bellowed ampoule, $V_0$ is the initial volume of the filled reservoir, and n is the number of half folds, or panels 50, 52 in ampoule 14 of fluid-delivery apparatus 10.

It is also appreciated that the length of the bellowed ampoule will be greater than a conventional cylindrical apparatus having the same volume of medicament in its cavity. For example, in a cylindrical apparatus of 3 mL volume and radius of 0.5 cm would have a length $L_c$ of 3.8 cm. The length of a 3 mL capacity bellowed ampoule of the same radius is determined according to the following equation:

$$L = \frac{L_c}{1 - Err(z_0)} \quad (4)$$

Hence, from the Equations (1) and (2), it is calculated that the length L of the bellowed ampoule is about 5.1 cm.

Figure 10:
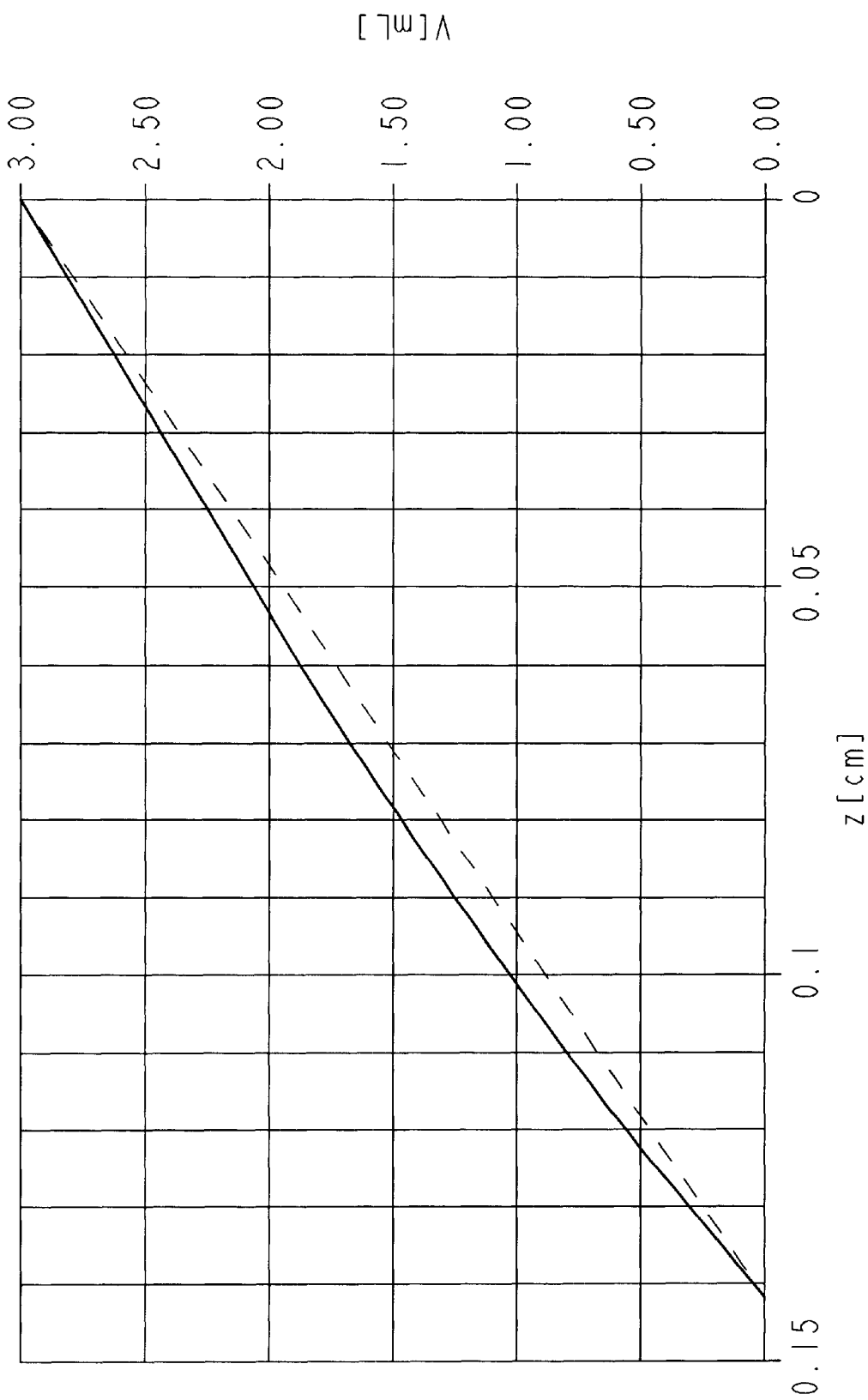
FIG. 10 is a plot of dispensed volume versus compression of the piston.

Using the above equations, a plot of the dispensed volume of medicament 56 versus the compression of ampoule 14 is shown in FIG. 10. The x-axis of the plot is the compression of piston 16 along axis 15 and the y-axis is the dispensed volume from ampoule 14 in mL. In addition, the hatched line is a reference line of a conventional cylindrical apparatus with linear dispense and the solid line corresponds to apparatus 10 with ampoule 14, each drawn from the respective start point ($z_0$, 0 mL dispensed volume) to the finish point (z=0 cm, 3 mL dispensed volume). By comparing the hatched and solid lines, it is apparent that the delivery behavior of apparatus 10 is nonlinear. Given this nonlinearity of dispense, scale 18 is constructed in accordance with Equation (3). As shown in FIG. 3, for apparatus 10, monotonic indicia 80 at 0.3 mL increments are placed along axis 15 in a manner that corresponds with the non-linear dispense of ampoule 14. Thus, a user is free to select and/or monitor an intermediate amount of medicament 56 dispensed from apparatus 10, which is less than the total amount of medicament 56 contained in cavity 54.

A manufacturer constructs apparatus by inserting end 44 of body 38 into passageway 30 so that travel limit 36 is aligned with opening 34. When ampoule 14 is pushed into passageway 30 of housing 12, taper 40 of tab 66 engages opening 34 of housing 12, pushing tab 66 in a radially inward direction. This pressure causes radially inward movement of sleeve 59 in opening 34. Furthermore, the axially inward movement of ampoule 14 into passageway 30 following the engagement of tab 66 with opening 34 forces end 44 of body 38 to engage seat 32 and tab 66 to engage end 20 of housing 12. See FIGS. 1 and 2. Thus, housing 12 is captured between tab 66 of travel limit 36 and end 44 of body 38 and a liquid and vapor seal is established and maintained between ampoule 14 and end 20 of housing 12.

To position indicia 80 in appropriate positions on housing 12, the manufacture must determine the relationship between the compression of ampoule 14 and the corresponding amount of fluid delivered. It is assumed that ampoule 14 is positioned housing 12 having a radius of $r_0$ that is substantially equal to an outermost radius of ampoule 14. To determine this relationship, the manufacturer first calculates the relative encroachment function Err of the bellowed ampoule from the equation $$Err = \Psi \cdot (1-\Psi/3), \text{ where } \Psi \equiv (c/r_0)\sqrt{1-(z/c)^2},$$

z is the height of one half-fold of one bellow of the ampoule, and c is length of an upper panel of one bellow. The manufacturer then determines the cumulative volume dispensed $V_d$ from the bellowed ampoule from the equation $$V_d = V_0 - (\pi r_0^2 nz) \cdot [1-Err],$$

where $V_0$ is the initial volume of the filled reservoir and n is the number of half folds in the bellowed ampoule.

Before delivering medicament 56 from apparatus 10, the user removes a seal (not shown) from lower surface 62 of travel limit 38. Piston 16 is then pressed toward travel limit 36 to force medicament 56 from ampoule 14 and through channel 64. Pressing piston 16 distributes pressure evenly throughout bellows 48, forcing medicament 56 through channel 64 and causing bellows 48 to fold upon one another about travel limit 36. See FIG. 2. The user may dispense a pre-determined volume of medicament 56 from ampoule 14 by pressing piston 16 in passageway 30 to a position adjacent to indicia 80 that corresponds with the pre-determined volume. Thus, apparatus 10 enables users to dispense various accurate doses of medicament 56 from ampoule 14, which are less than the total amount of medicament 56 contained within ampoule 14.

Enlarged views of alternative embodiments of ampoules 114, 130 that are suitable for use with housing 12 and piston 16 are shown in FIGS. 4 and 5 respectively.

Ampoules 114, 130 are similar to ampoule 14 illustrated in FIGS. 1–3, except that ampoules 114, 130 include micropores 118. Micropores 118 have a diameter 120 sized to enable gases, such as air to escape from cavity 54, while preventing medicament 56 from traveling into passageway 30 of housing 12. It is appreciated that while micropores 118 may be formed by injection molding, may be punched through the material of ampoule, or may be formed in any number of manners in accordance with this disclosure. In addition, while micropores 118 are shown to extend in a linear direction, micropores 118 may take on any number of curved paths. As shown in FIG. 4, micropores 118 of ampoule 114 extend through upper panel 52 of body 38. Micropores 118 of ampoule 130, as shown in FIG. 5, extend through closed end 42. Micropores 118 may be formed in ampoules 114, 130 in greater or fewer than one location in accordance with this disclosure. For example, it is contemplated that micropores may be formed through lower panel 50, corners 53, 55, and sleeve 59 in accordance with this disclosure.

An alternative embodiment of a fluid-delivery apparatus 210 is shown in FIG. 6 that enables a user to deliver fluids precisely. Apparatus 210 includes an ampoule 214 that is similar to ampoule 14, except that it includes a tube 216 extending from end 42 and a travel limit 236 with flexible tabs 222 positioned at lower surface 62 of sleeve 59. It is appreciated that the source of lost volume of ampoule 214, relative to the case of a smooth-bore cylinder such as housing 12 having a substantially equivalent radius, remains the movement of panels 50, 52. Therefore, the encroachment function Err for apparatus 210 and the positioning of scale 18 on housing 12 is calculated as discussed above with reference to apparatus 10.

Tube 216 of ampoule 214 defines a passage 218 in communication with a check valve 220 that regulates the passage of gases, such as air from ampoule 214. In addition, housing 12 of apparatus 210 includes ports 212 to vent gases, such as air, out of passageway 30. Tube 216 of ampoule 214 is sized for extension through a channel 215 that extends through base 68 and rod 70 of piston 16. It is appreciated that channel 215 may take on any number of curved paths through base 68 and rod 70. It is also appreciated that channel 214 may be formed to extend for various lengths through piston 16 and may be formed to have a variety of widths. Ampoule 214 may include greater than one tube, piston 16 may include a corresponding number of channels, and the number of ports through housing 12 may vary in accordance with this disclosure.

Tabs 222 of travel limit 236 cooperate with end 20 of housing 12 to permit limited movement between ampoule 214 and housing 12. Each tab 222 has a tapered portion 224 that flexes during assembly and a flat retainer portion 226 facing housing 12. As shown in FIG. 6, travel limit 236 communicates with a check valve 228 via an infusion line 230. When in the closed position, check valve 228 prevents medicament 56 from flowing through line 230. When piston 16 moves toward travel limit 236, fluid pressure moves check valve 228 to an open position to allow medicament 56 to flow from apparatus 210. Check valve 228 also cooperates with check valve 220, so that as piston 16 travels in passageway 30, gasses present in ampoule 214 escape through tube 216 and past check valve 220. While line 230 is illustrated, any number of syringes, tubes, reservoirs, or the like may be communicate with sleeve 59 and check valve 228 to direct the flow of medicament 56 from ampoule 14 in accordance with this disclosure.

To assemble apparatus 210, end 44 of ampoule 214 is inserted into passageway 30 so that travel limit 236 is aligned with opening 34. When ampoule 214 is pushed into passageway 30, taper 224 engages housing 12, pushing tab 222 in a radially inward direction. This pressure causes radially inward movement of sleeve 59. Additional movement of ampoule 214 in passageway 30 following the engagement of tab 222 with housing 12 forces end 44 of body 38 to engage seat 32. Thus, ampoule 214 is held in housing 12 by a friction fit between sleeve 59 and a rim of opening 34.

To dispense medicament 56 from apparatus 210, the user presses piston 16 toward travel limit 236, forcing medicament past check valve 228. Pressing piston 16 distributes pressure evenly throughout ampoule 214, causing bellows 48 to fold upon one another about travel limit 236. This pressure also causes any gases present within ampoule 214 to flow through tube 216 and past check valve 220. The user may dispense a pre-determined volume of medicament 56 from ampoule 214 by depressing piston 16 to a position adjacent to indicia 80 (FIG. 3) that corresponds with the pre-determined volume. Thus, apparatus 210 enables users to dispense various accurate doses of medicament from ampoule 214.

Figure 7:
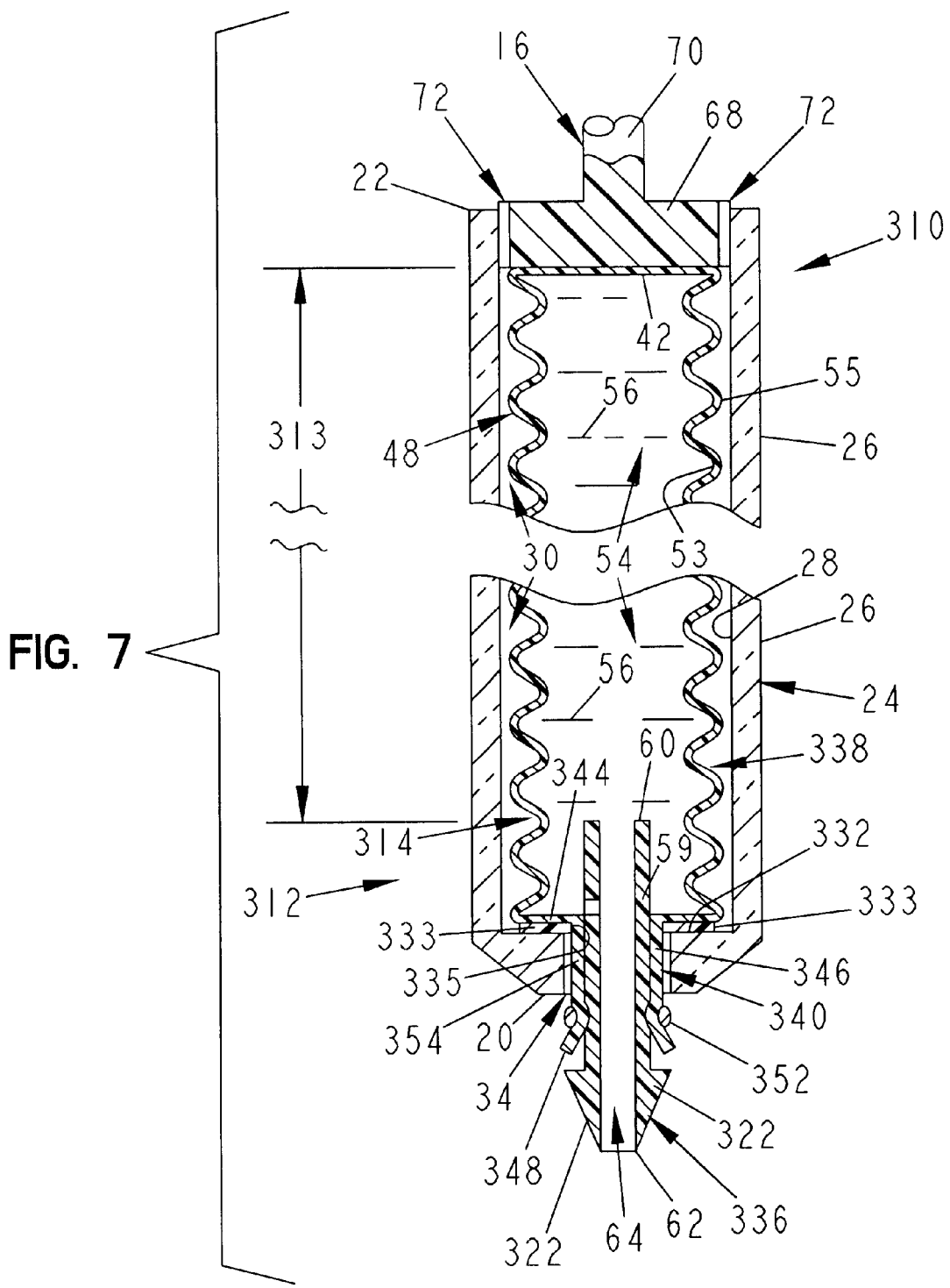
FIG. 7 is a cross-sectional view of another embodiment of the present invention.

Referring now to FIG. 7, an alternative embodiment of a fluid-delivery apparatus 310 is provided that enables a user to deliver fluids precisely. Apparatus 310 is similar to apparatus 10, except for the connection between a housing 312 and a bellowed ampoule 314. It is appreciated that the source of lost volume of ampoule 314, relative to a smooth bore cylinder, of substantially equivalent radius, remains the movement of panels 50, 52. Therefore, the encroachment function Err and the positioning scale 18 on housing 12 is calculated as discussed above with reference to apparatus 10.

Housing 312 of apparatus 310 includes a seat 332 that extends generally perpendicular to interior surface 28 of wall 24. Additionally, end 20 of housing 312 is formed to extend generally parallel to seat 332. As shown in FIG. 7, ampoule 314 is positioned in passageway 30 and formed to dispense a pre-determined volume of medicament from housing 312. Ampoule 314 includes a body 338 and a neck 340 extending from body 338. Body 338 includes an end 344 coupled to a rigid plate 333 and is positioned upon seat 332. Plate 333 is coupled to body 338 with a commercially available adhesive suitable for adhering two plastic components together. Plate 333 includes an aperture 335 that is aligned with opening 334 and is constructed of a rigid plastic, however it is appreciated that plate 333 may be formed of a variety of materials such as glass, ceramics, or metals in accordance with this disclosure. It is also appreciated that various fasteners such as hook and loop, snaps, and the like may be used to couple body 338 and plate 333 together in accordance with this disclosure.

Neck 340 of ampoule 314 includes a fixed end 346 extending from end 344 of body 338, an opposite free end 348 positioned outside of housing 312, and a center portion 350 extending through opening 334. Neck 340 extends through aperture 335 and is coupled to travel limit 336 by a clamp 352 adjacent to free end 348. Clamp 342 is illustratively a static seal, although it is appreciated that a variety of traditional seals, adhesives, clamps, and the like may be used to couple neck 340 to travel limit 336 in accordance with this disclosure.

To assemble apparatus 310, a manufacturer couples plate 333 to end 344 of body 338 with an adhesive (not shown). Travel limit 336 is then inserted through free end 348 of neck 340, past aperture 335 of plate 333, and into cavity 54. A seal is formed between travel limit 336 and neck 340 by extending clamp 352 about neck 340 and travel limit 336. End 344 of body 338 is then inserted into passageway 30 so that travel limit 336 is aligned with opening 334. When ampoule 314 is pushed into passageway 30 of housing 312, a tapered portion 322 of travel limit 336 engages housing 312 and presses travel limit 336 in a radially inward direction. Further, the axially inward movement of ampoule 314 into passageway 30 positions plate 333 on seat 332. Thus, ampoule 314 is held in housing 12 by the engagement between plate 333 and housing 312 and a friction fit between neck 340 and a rim of opening 334.

To dispense medicament from apparatus 310, the user presses piston 16 toward travel limit 336 to force medicament through channel 64. Piston 16 is free to travel a distance 313 defined by the length that travel limit 336 extends into cavity 54 of ampoule 314. Pressing piston 16 distributes pressure evenly throughout bellows 48, forcing medicament 56 through channel 64 and causing bellows 48 to fold upon one another about travel limit 336. The user may dispense a pre-determined volume of medicament 56 from ampoule 314 by depressing piston 16 in passageway 16 to a position adjacent to indicia 80 (FIG. 3) that corresponds with the pre-determined volume. Thus, apparatus 310 enables users to dispense various accurate doses of medicament from ampoule 314.

While embodiments of a manual fluid-delivery apparatus have been discussed above, it is appreciated that apparatuses 10, 210, 310 may be formed for use in a motorized mode of operation. For purposes of clarity, only apparatus 10 will be discussed hereafter with reference to this motorized mode operation, although the following description applies equally to both apparatus 210 and apparatus 310. Moreover, it is appreciated that apparatus 10 when used in apparatus 410 need not include visible monotonic scale 18.

Figure 8:
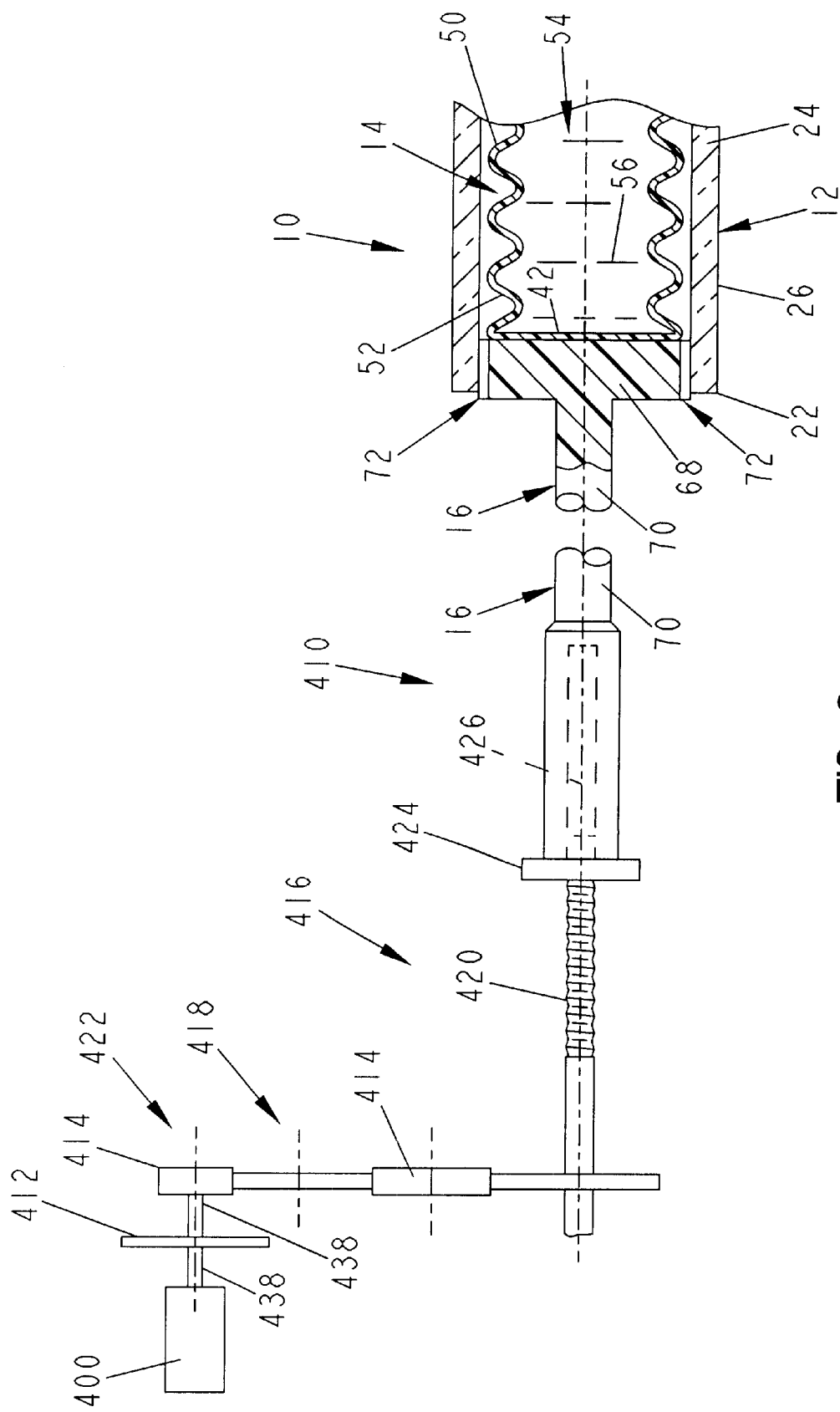
FIG. 8 is a diagrammatic view of another embodiment of the present invention, showing a fluid-delivery apparatus and a piston-drive system.
Figure 9:
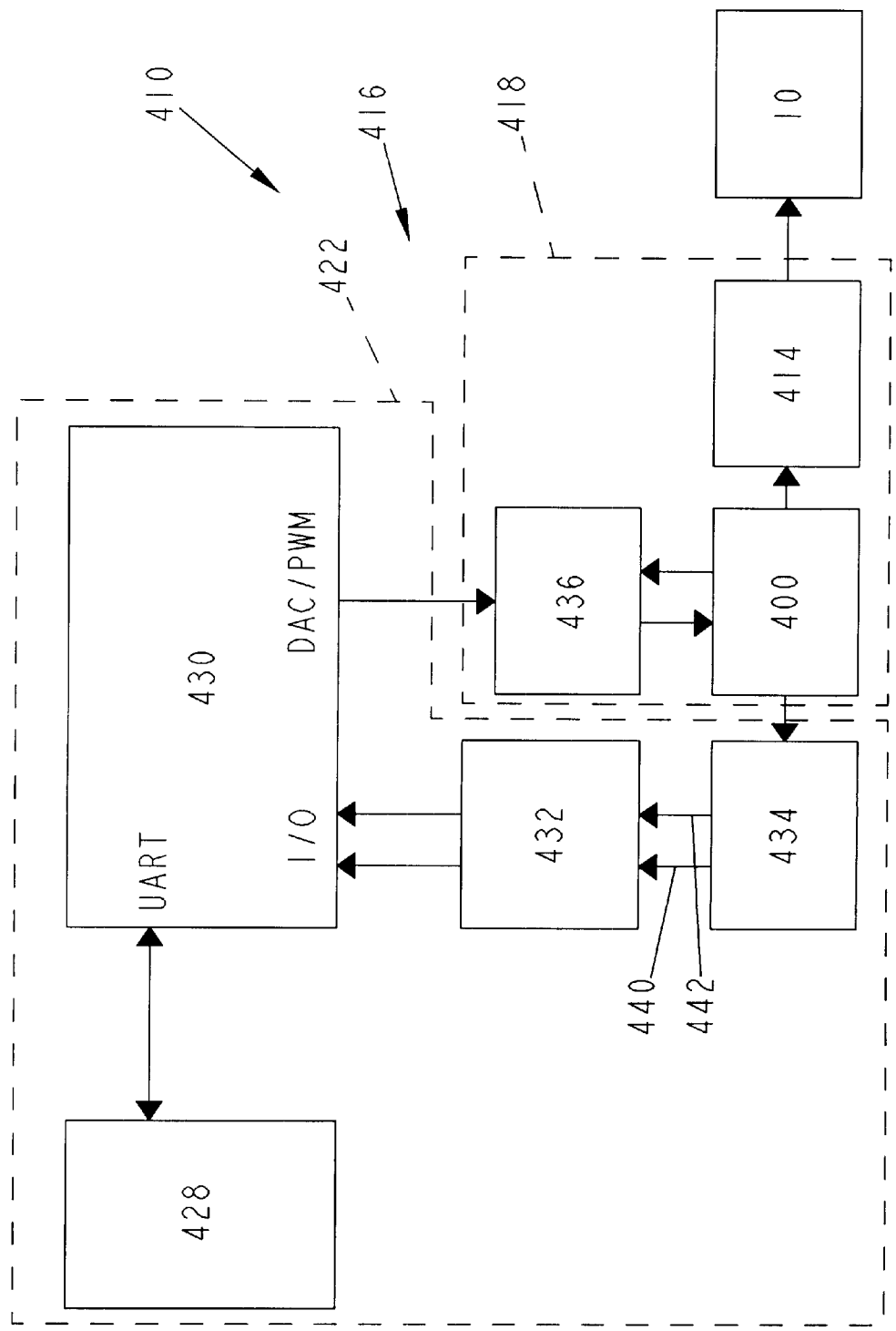
FIG. 9 is a diagrammatic view of the piston-drive system of FIG. 8 showing the piston-drive system including a torque-production system and an actuator system.

Motorized fluid-delivery apparatus 410 is shown in FIGS. 8 and 9. Apparatus 410 includes fluid-delivery apparatus 10 and a piston-drive system 416 that is configured to apply a force to piston 16 to dispense medicament 56 from apparatus 10. System 416 includes a torque-production system 418 and an actuator system 422. As shown in FIG. 8, torque-production system 418 includes a gear train 414 turned by an electric motor 400 and formed to apply a torque to a lead screw 420 to move drive nut 424 about an axis 426 into engagement with piston 16 of apparatus 10. Motor 400 is actuated by a motor driver 436 (FIG. 9) and communicates with gear train 414 via a motor shaft 438.

As shown in FIG. 9, actuator system 422 includes a host computer 428, a controller 430, a quadrature detector and counter 432, and a two-phase encoder 434 coupled to motor 400 via motor shaft 438. Since computer 430, quadrature detectors and counters 432 and encoders 434 are known and readily available in the marketplace, their structure and operation will not be described herein. Host computer 428 computes the encroachment function Err as discussed above with reference to apparatus 10 and progressively drives piston 16 by increasing stroke displacements to maintain constant successive stroke volumes.

A constant series of motor-encoder counts would cause piston 16 to move at a constant rate through housing 12, resulting in the bowed plot of the solid line in FIG. 10. Departure from this constant series of encoder counts, as discussed below, obviates this bowed plot and allows for a liner dispense of medicament 56 from ampoule 14.

A derivative with respect to displacement z of dispensed volume $V_d$ is as follows:

$$\frac{dV_d}{dz} = -\pi n \cdot \left[ r_0^2 \cdot [1 - \psi(1 - \psi/3)] + \left( \frac{1 + 2\psi/3}{\psi} \right) \cdot z^2 \right], \quad (5)$$

where $$\Psi \equiv (c/r_0)\sqrt{1-(z/c)^2} \quad (2)$$

Referring now to FIG. 3b, a displacement $\Delta z$ of ampoule 14 along axis 15 is equivalent (proportional by gear-ratio choice) to a number of motor encoder counts. The terms $\Delta z$ and motor encoder counts m will hereafter be used equivalently in discussion. An expression for the derivative of displacement z with respect to dispensed volume $V_d$ to extract the encoder linearization function for differential dispense volumes is as follows:

$$dz/dV_d = \quad (6)$$

$$\left( \frac{1}{\frac{dV_d}{dz}} \right) = \left( -\pi n \cdot \left[ r_0^2 \cdot [1 - \psi(1 - \psi/3)] + \left( \frac{1 + 2\psi/3}{\psi} \right) \cdot z^2 \right] \right)^{-1}$$

Figure 11:
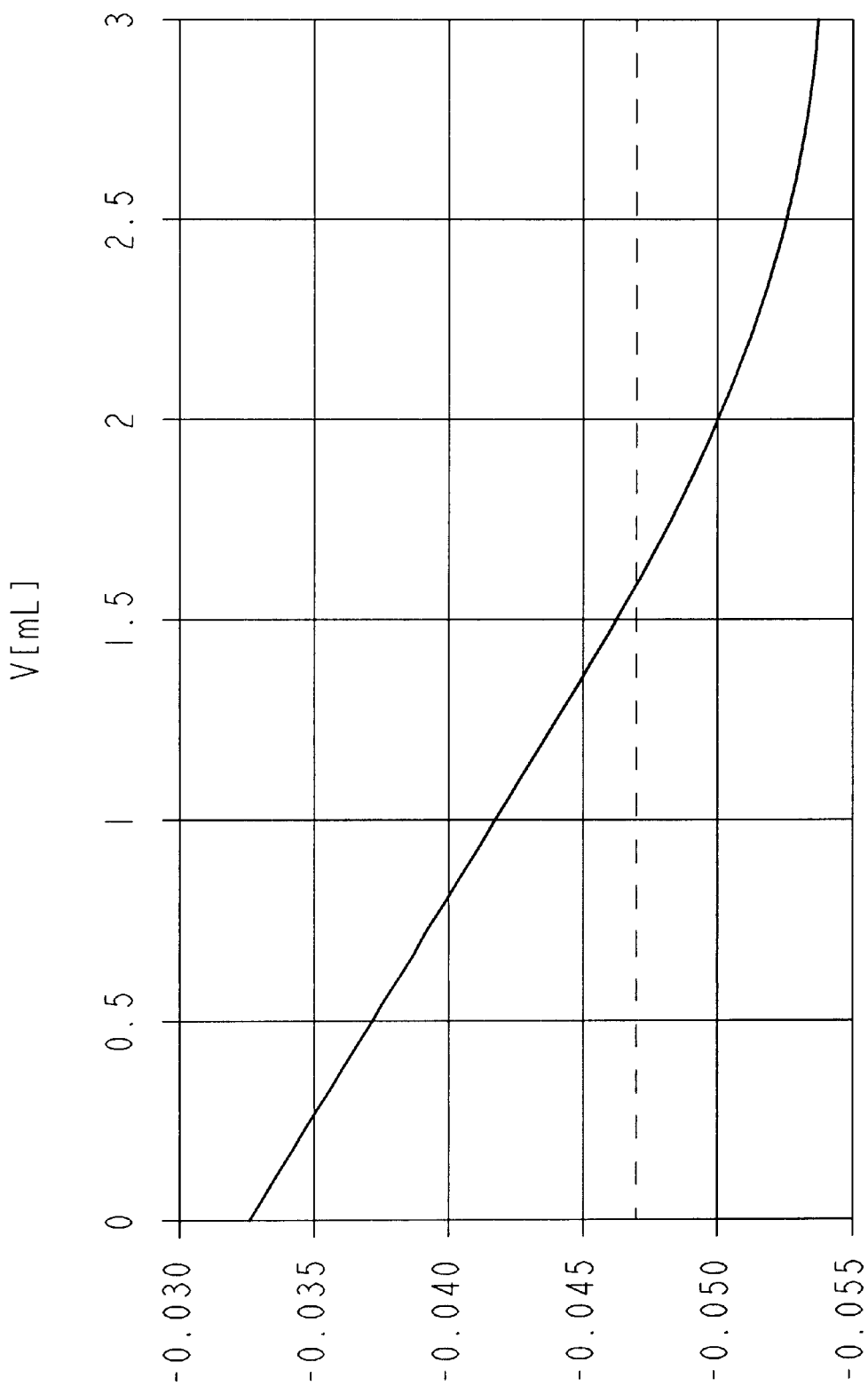
FIG. 11 is a plot of the derivative dz/dV versus volume displacement.
Figure 12A:
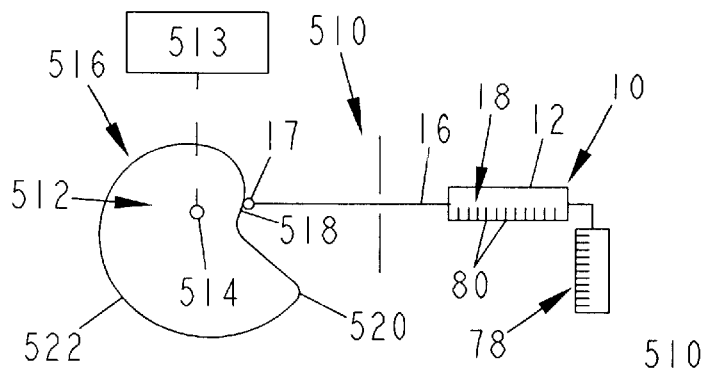
FIGS. 12a–12j are diagrammatic views of another embodiment of the present invention.
Figure 12B:
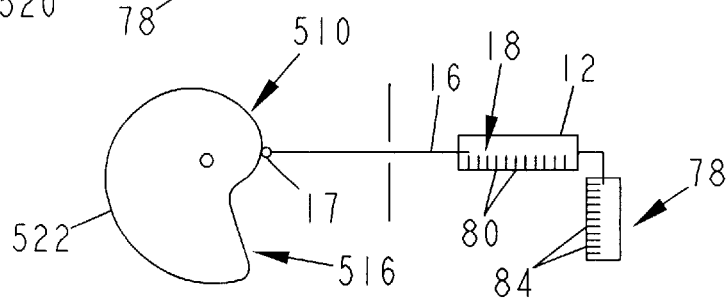
Figure 12C:
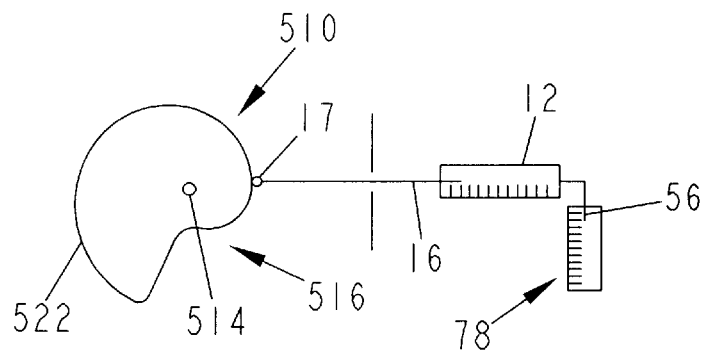
Figure 12D:
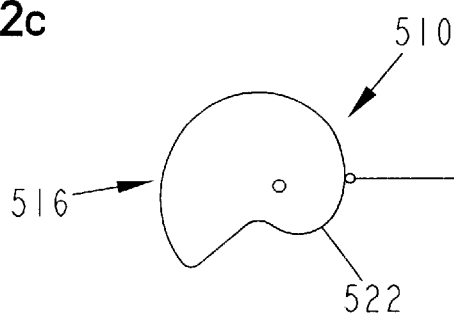
Figure 12E:
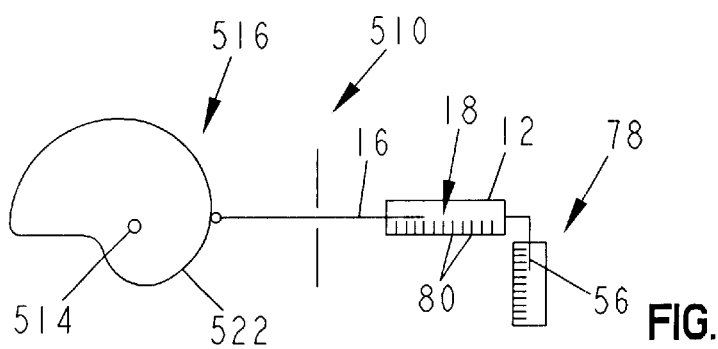
Figure 12F:
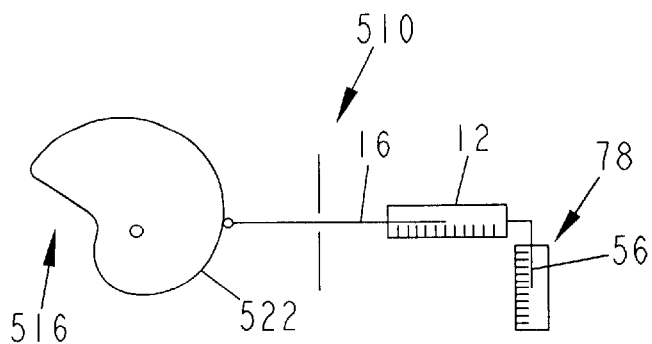
Figure 12G:
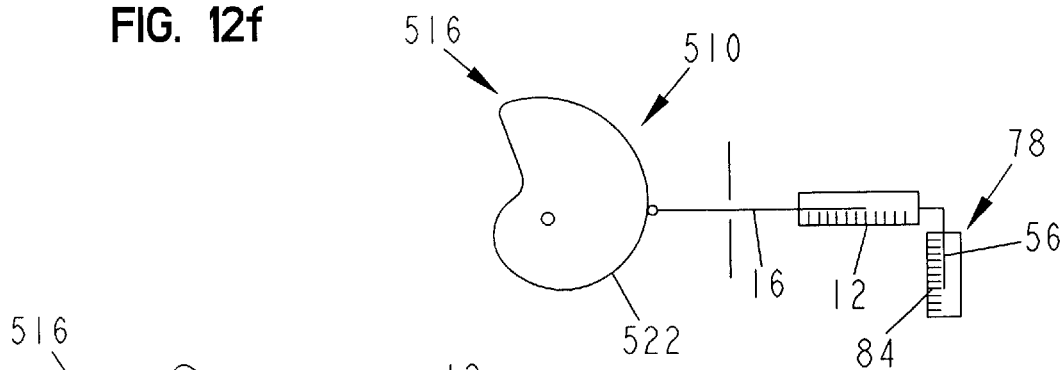
Figure 12H:
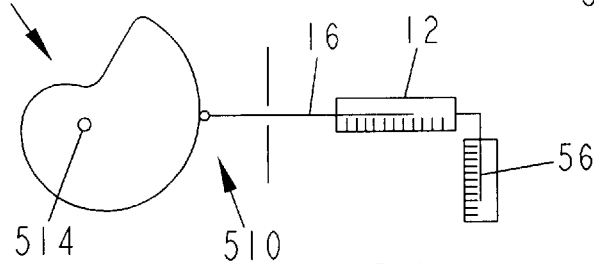
Figure 12I:
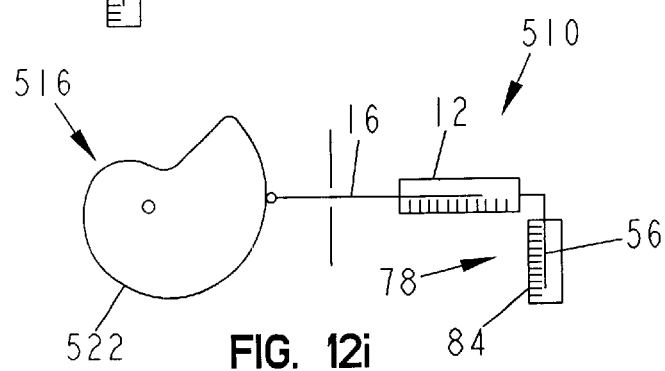
Figure 12J:
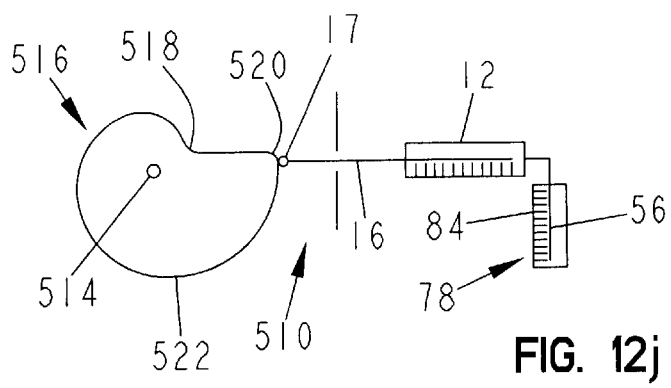

A plot of $dz/dV_d$ is set out in FIG. 11 and illustrates how a constant differential in dispensed volume can be achieved at any value of compression z. In the plot of FIG. 11, the x-axis corresponds with the volume medicament dispensed from ampoule 14 and the y-axis corresponds with values of the derivative $dz/dV_d[1/(cm*cm)]$. The hatched reference line in FIG. 10, which corresponds to linear delivery of medicament appears in FIG. 11 as a constant slope of $-0.04714/cm^2$ under the assumption that $V_O=3$ mL and $z_0=c/\sqrt{2}$, where c=0.2 cm.

Ampoule 14 requires a tailored change in encoder counts to dispense a constant volume of medicament, depending on the current location of piston 16 in housing 12. Motor-encoder counts m can be adjusted to dispense successive equal volumes of fluid from ampoule 14 so that $$\frac{\Delta m}{\Delta V_d} = \text{constant.}$$

A displacement of the piston dL tracked by the shaft-angle encoder dθ at motor 400 corresponds to a number of encoder counts $dm=\alpha_1 d\theta$. It is appreciated that the term $\alpha_1$ depends on the resolution of the encoder; e.g. twelve ticks per 360° (revolution) gives $12/360=\alpha_1=0.333$. The lead-screw pitch and the gear train introduce additional proportionality factors between the encoder counts and are included in the term $\alpha_2$. Piston displacement dL is n times larger than dz, because there are n folds in the bellows length. All together, the encoder counts dm are proportional to the compression dz by the following expression:

$$dm = \alpha_1 \cdot \alpha_2 \cdot n \cdot dz. \quad (7)$$

Referring again to FIG. 11, it is shown that the encoder counts m must increase by about 50% to deliver the same differential volume $dV_d$ near the end of piston 16 travel, compared with delivering the same volume at the start of piston 16 travel. During the first, 1.5 mL of dispensed volume, the increase in piston travel or encoder counts, per successive volume differential, must increase by an almost constant amount per stroke. Each stroke is longer than the previous by an almost fixed amount. After this halfway point of total piston travel, the increase in piston travel lessens per stroke until a saturation value is finally reached.

As FIG. 10 shows, the slope of the linear delivery (re hatched reference line) must have generally the same slope as the nonlinear delivery of apparatus 10 in the vicinity of 1.5 mL. This observation is consistent with the intersection of the hatched line with the solid line in FIG. 11. For finite volume delivery increments $\Delta V_d$, the function plotted in FIG. 10 is used directly. This function is given by Equation (5).

The manufacturer constructs torque-production system 418 and an actuator system 422 in a manner that is well known to one of ordinary skill in the art. To dispense a constant volume of medicament 56 from ampoule 14 using apparatus 410, the manufacturer must determine the relative encroachment function Err of the bellowed ampoule and the cumulative volume dispensed $V_d$ from the bellowed ampoule as discussed above with reference to apparatus 10. Also, the manufacturer determines the rate of change of compression of the ampoule with respect to a constant linear flow of medicament 56 from ampoule 14 from the equation $$dz/dV_d = \left(\frac{1}{\frac{dV_d}{dz}}\right) = \left(-\pi n \cdot \left[r_0^2 \cdot [1 - \psi(1 - \psi/3)] + \left(\frac{1 + 2\psi/3}{\psi}\right) \cdot z^2\right]\right)^{-1}, \text{ where}$$

$$\Psi \equiv (c/r_0)\sqrt{1-(z/c)^2}.$$

Once this encoder linearization function is established, the manufacturer determines the proportionality between the encoder counts dm and the compression dz of ampoule 14 from the equation $dm = \alpha_1 \cdot \alpha_2 \cdot n \cdot dz$, where $\alpha_1$ is the resolution of the encoder and $\alpha_2$ is the proportionality factor of the lead-screw pitch and the gear train.

To dispense medicament from apparatus 410, the user actuates motor 400, which rotates encoder 434 in one direction. By convention, a repetitive sequence of quadrature state values are transmitted to quadrature detector and counter 432 via lines 440, 442 when encoder 434 rotates. The detector uses the signals on lines 440, 442 to determine the direction of rotation of encoder 434 and forwards these signals to controller 430. Controller 430 then interacts with computer 428, which calculates the amount of encroachment of ampoule 14 and the forwards positional information back to controller 430. Controller 430 then signals motor driver 436 to move motor 400 a distance that is based upon the encroachment function calculations of computer 428.

Additionally, the counter is preferably a bidirectional counter in the form of an up/down counter and accumulates the number of rotation pulses associated with the signals on lines 440, 442 from encoder 434. Once medicament 56 has been emptied from ampoule 14, shaft 438 rotates in a reverse direction to return nut 424 to a starting position on screw 420. Since shaft 438 is operatively coupled with encoder 434, shaft 438 mechanically transmits the reverse rotation to encoder 434. Upon reverse rotation, encoder 434 causes a sequential reversal of the quadrature state values transmitted to quadrature detector and counter 432 on lines 440, 442 and the count accumulated in the forward direction is decremented by the reverse direction pulses.

Still further, as shown by FIGS. 12a–12j, a motorized fluid-delivery apparatus 510 is provided in accordance with another embodiment of the present invention. It is appreciated that apparatuses 10, 210, 310 may be formed for use in apparatus 510. For purposes of clarity, only apparatus 10 will be discussed hereafter with reference to this motorized mode operation, although the following description applies equally to both apparatus 210 and apparatus 310. Moreover, it is appreciated that apparatus 10 when used in apparatus 410 need not include visible monotonic scale 18.

Motorized apparatus 510 includes fluid-delivery apparatus 10 and piston-drive system 516. Piston-drive system 516 includes a motor 513 (FIG. 12a) coupled to a cam 512 via a drive shaft 514. Cam 512 includes a ramped surface 522 that changes in radius to dispense successive equal volumes of medicament from housing 12. As shown in FIGS. 12a–12j, cam surface includes a first part 518, a second part 520, and a ramp 522 extending between parts 518, 520. The radius of cam surface 516 increases as ramp 522 extends from first part 518 toward second part 520 so that piston 16 is pressed further into housing 12 as cam 512 rotates on drive shaft 514.

In operation, cam 512 rotates in a clock-wise manner on shaft 514. As cam 512 rotates, ramp 522 presses head 17 of piston 16 a pre-determined distance away from shaft 514 and into housing 12. Since ramp 522 slopes in a non-linear manner, the rate of travel of piston 16 through housing 12 will also be non-linear. As shown diagrammatically in FIGS. 12a–12j, the amount of travel of piston 16 between monotonic indicia 80 will vary from indicia 84 of linear scale 78 to account from the reduction in volume of cavity 54 of ampoule 14 verses the volume of passageway 30 of housing 12.

The relationship $$\frac{\Delta z}{\Delta V_d}$$

=constant of ampoule 14 can be achieved by use of cam drive 512. The shape of cam 512 having a radius r is defined as follows:

$$r = r_1 + \Delta r(\theta) = r_1 + \Delta r_2(\theta) + \Delta r_3(\theta), \tag{8}$$

where $r_1$ is the initial value of the cam radius, $$r_2 = L_0\left(\frac{\theta}{2\pi}\right)[L_0 = nz_0, \text{ initial ampoule length}],$$

and $r_3$, a nonlinear term as will be described below.

The piston serves as a cam follower; i.e., the cam drives the piston head so that:

$$\Delta r = -n\Delta z \tag{9}$$

From Equation (9) it is shown that the displacement $n\Delta z$ in the position variable nz is advanced relative to the displacement provided by the linear terms alone. The change in magnitude of the radius, due to nonlinearity, may be expressed as follows:

$$\Delta r_3 = -n \cdot [z_2 - z_1], \tag{10}$$

where $z_1 = z_1(\theta)$ is the linear-dispense position and $z_2$ is the nonlinear-dispense position.

For each value of $z_1$, where $$z_1 = z_0(1 - \theta/2\pi), \quad (11)$$

there is a corresponding volume:

$$V = V(z_1) = V_0(1 - z_1/z_0) \quad (12)$$

Corresponding to this same volume $V(z_1)$, there is a unique, larger value $z_2$. This value $z_2$ must be found numerically according to a suitable interpolation algorithm, because the nonlinear function $V = V(z_2)$ given by Equation (5) cannot be inverted to find $z_2 = V^{-1}(z_2)$ in closed mathematical form (analytically). The precision requirements on the interpolation algorithm are severe, on the order of sub-microns.

The result of sampling many values of $z_1$ according to Equation (11) allows [tabular] generation of the desired function. A sample tabulation of the nonlinear term of the cam function $\Delta r_3 = -n(z_2 - z_1) = -n[z_2 - z_1(\theta)]$ is shown below in Table 1.

TABLE 1

| Cam-shaft angle $\theta$[radians] | $nz_1$ | $\Delta r_3 = -n[z_2 - z_1]$ |
| --- | --- | --- |
| 0 | 0.00000 | 0.00000 |
| π/4 | 0.64190 | −0.12829 |
| π/2 | 1.28379 | −0.21158 |
| 3π/4 | 1.92569 | −0.25247 |
| π | 2.56759 | −0.25464 |
| 5π/4 | 3.20949 | −0.22319 |
| 3π/2 | 3.85138 | −0.16472 |
| 7π/4 | 4.49328 | −0.08726 |
| 2π | 5.13518 | 0.00000 |

Note the retardation of the radius [negative values of $\Delta r_3$] and the corresponding advance [increase in value] of z coordinate given by Equation (11). The nonlinear term vanishes at the start and end of delivering the total volume contained in the bellowed ampoule.

A sample calculation of the equation $r = r_1 + \Delta r(\theta) = r_1 + \Delta r_2(\theta) + \Delta r_3(\theta)$, at 10-degree increments accurate to 1 picometer is provided in Table 2. The constant increment of volume delivery is 8.33 microliter, with 10-degree rotation steps. Angles other than those listed here can be calculated by the method outlined in the previous subsection, to yield any desired magnitude of constant increment in volume delivery.

TABLE 2

| Theta [degrees] | Theta [radians] | r1 [cm] | Delta r2 [cm] | Delta r3 [cm] | Radius [cm] | Volume [mL] |
| --- | --- | --- | --- | --- | --- | --- |
| 0 | 0.000000 | 2 | 0.00000 | 0.00000 | 2.00000 | 0.00000 |
| 10 | 0.174533 | 2 | 0.14264 | −0.03254 | 2.11011 | 0.08333 |
| 20 | 0.349066 | 2 | 0.28529 | −0.06272 | 2.22257 | 0.16667 |
| 30 | 0.523599 | 2 | 0.42793 | −0.09064 | 2.33730 | 0.25000 |
| 40 | 0.698132 | 2 | 0.57058 | −0.11630 | 2.45427 | 0.33333 |
| 50 | 0.872665 | 2 | 0.71322 | −0.13972 | 2.57350 | 0.41667 |
| 60 | 1.047198 | 2 | 0.85586 | −0.16094 | 2.69492 | 0.50000 |
| 70 | 1.221730 | 2 | 0.99851 | −0.17998 | 2.81853 | 0.58333 |
| 80 | 1.396263 | 2 | 1.14115 | −0.19684 | 2.94431 | 0.66667 |
| 90 | 1.570796 | 2 | 1.28379 | −0.21158 | 3.07222 | 0.75000 |
| 100 | 1.745329 | 2 | 1.42644 | −0.22423 | 3.20221 | 0.83333 |
| 110 | 1.919862 | 2 | 1.56908 | −0.23479 | 3.33429 | 0.91667 |
| 120 | 2.094395 | 2 | 1.71173 | −0.24335 | 3.46838 | 1.00000 |
| 130 | 2.268928 | 2 | 1.85437 | −0.24992 | 3.60445 | 1.08333 |
| 140 | 2.443461 | 2 | 1.99701 | −0.25453 | 3.74248 | 1.16667 |

TABLE 2-continued

| Theta [degrees] | Theta [radians] | r1 [cm] | Delta r2 [cm] | Delta r3 [cm] | Radius [cm] | Volume [mL] |
| --- | --- | --- | --- | --- | --- | --- |
| 150 | 2.617994 | 2 | 2.13966 | −0.25727 | 3.88239 | 1.25000 |
| 160 | 2.792527 | 2 | 2.28230 | −0.25817 | 4.02413 | 1.33333 |
| 170 | 2.967060 | 2 | 2.42495 | −0.25726 | 4.16768 | 1.41667 |
| 180 | 3.141593 | 2 | 2.56759 | −0.25464 | 4.31295 | 1.50000 |
| 190 | 3.316126 | 2 | 2.71023 | −0.25036 | 4.45987 | 1.58333 |
| 200 | 3.490659 | 2 | 2.85288 | −0.24445 | 4.60842 | 1.66667 |
| 210 | 3.665191 | 2 | 2.99552 | −0.23704 | 4.75849 | 1.75000 |
| 220 | 3.839724 | 2 | 3.13817 | −0.22816 | 4.91000 | 1.83333 |
| 230 | 4.014257 | 2 | 3.28081 | −0.21789 | 5.06292 | 1.91667 |
| 240 | 4.188790 | 2 | 3.42345 | −0.20633 | 5.21712 | 2.00000 |
| 250 | 4.363323 | 2 | 3.56610 | −0.19356 | 5.37253 | 2.08333 |
| 260 | 4.537856 | 2 | 3.70874 | −0.17965 | 5.52909 | 2.16667 |
| 270 | 4.712389 | 2 | 3.85138 | −0.16472 | 5.68667 | 2.25000 |
| 280 | 4.886922 | 2 | 3.99403 | −0.14884 | 5.84518 | 2.33333 |
| 290 | 5.061455 | 2 | 4.13667 | −0.13210 | 6.00457 | 2.41667 |
| 300 | 5.235988 | 2 | 4.27932 | −0.11464 | 6.16468 | 2.50000 |
| 310 | 5.410521 | 2 | 4.42196 | −0.09653 | 6.32543 | 2.58333 |
| 320 | 5.585054 | 2 | 4.56460 | −0.07787 | 6.48674 | 2.66667 |
| 330 | 5.759587 | 2 | 4.70725 | −0.05878 | 6.64846 | 2.75000 |
| 340 | 5.934119 | 2 | 4.84989 | −0.03938 | 6.81051 | 2.83333 |
| 350 | 6.108652 | 2 | 4.99254 | −0.01974 | 6.97280 | 2.91667 |
| 351 | 6.126106 | 2 | 5.00680 | −0.01777 | 6.98903 | 2.92500 |
| 360 | 6.283185 | 2 | 5.13518 | 0.00000 | 7.13518 | 3.00000 |
| 0 | 0.000000 | 2 | 0.00000 | 0.00000 | 2.00000 | 0.00000 |

Figure 13:
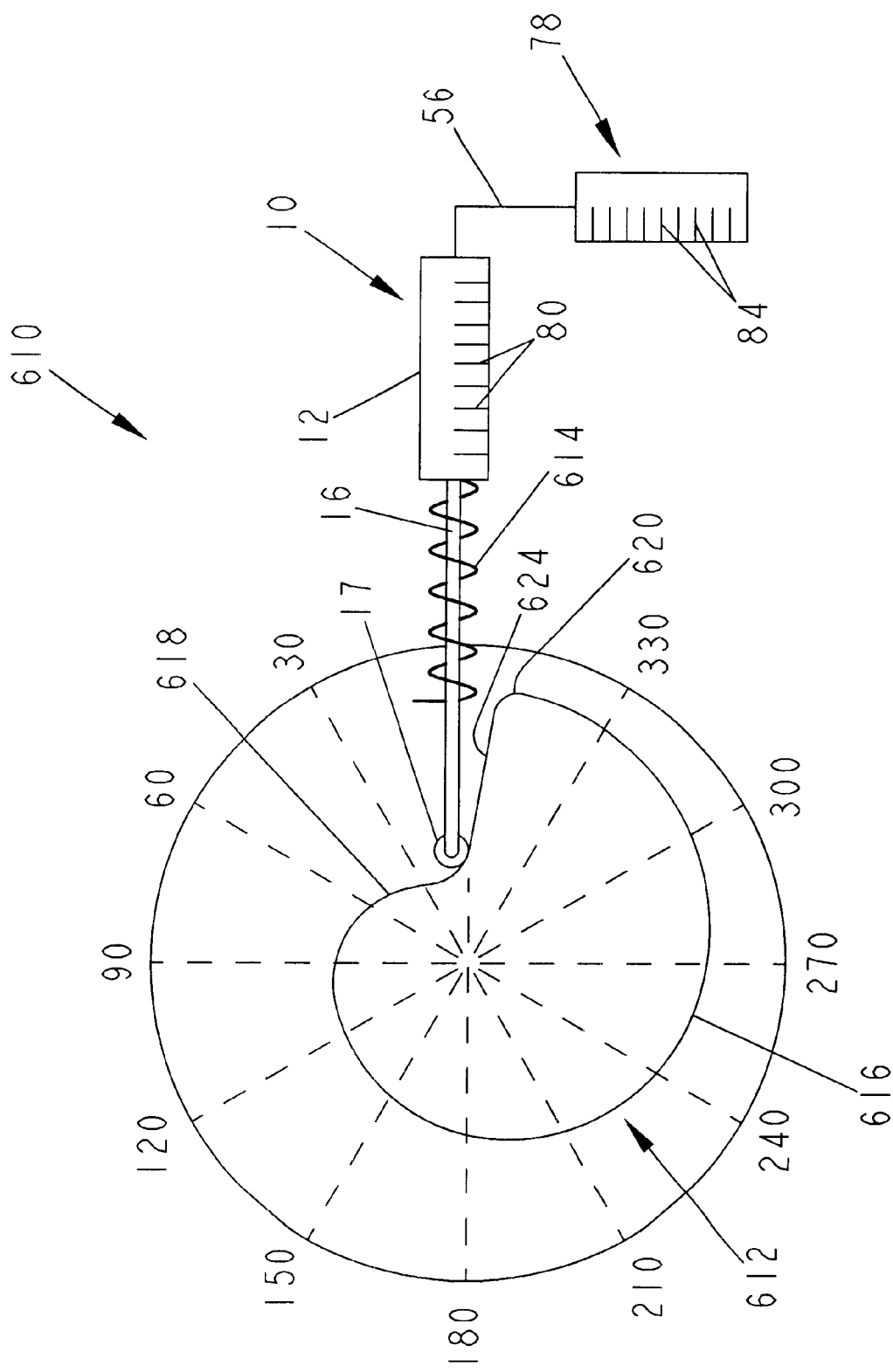
FIG. 13 is a diagrammatic view of another embodiment of the present invention.

An alternative embodiment of motorized fluid-delivery apparatus 610 is shown in FIG. 13. Motorized apparatus 610 is formed similarly to apparatus 510, except that it includes a cam 612 formed to rotate in one direction a full 360 degrees and a spring 614 extends about piston 16. Spring 614 drives piston head 17 into engagement with cam 612. It is appreciated that apparatuses 10, 210, 310 may be formed for use in apparatus 610. For purposes of clarity, only apparatus 10 will be discussed hereafter with reference to this motorized mode operation, although the following description applies equally to both apparatus 210 and apparatus 310. Moreover, it is appreciated that apparatus 10 when used in apparatus 410 need not include visible monotonic scale 18.

Cam 612 may be used to dispense successive equal volumes of medicament 56 from housing 12. Cam 612 includes a cam surface 616 that changes in radius to dispense successive equal volumes of medicament from housing 12. As shown in FIG. 13, cam 612 is formed similarly to cam 512, except that cam 612 includes a sloped portion 624 that extends between first and second parts 618, 620. This sloped portion 624 serves as a transition for piston head 17 as second part 620 of cam 612 rotates in a clock-wise direction between about the 30 degree position and the 330 degree position, shown in FIG. 13. The radius of ramp 616 of cam 612 is calculated in accordance with a suitable interpolation algorithm as discussed above with reference to cam 512.

In operation, as cam 612 rotates in a clock-wise manner, ramp 616 presses head 17 of piston 16 a pre-determined distance into housing 12. Since ramp 616 is non-linear, the rate of travel of piston 16 through housing 12 will also be non-linear similar to that shown in FIGS. 12a–12j. When, however, second part 620 of cam 612 travels past piston head 17, spring 614 presses head 17 along sloped portion 624 toward first part 618. Thus, the cyclical nature of cam 612 implies that the ampoule can automatically refill upon completion of its dispense function.

Although the invention has been described in detail with reference to a preferred embodiment, variations and modifications exist within the scope and spirit of the invention as described and defined in the following claims.

What is claimed is:

1. A fluid-delivery apparatus for delivering a medicament to a patient, the apparatus comprising:

a housing defining a passageway, a bellowed ampoule positioned to lie in the passageway of the housing, the bellowed ampoule including a body having first and second ends and formed to define a cavity configured to contain the medicament, a piston positioned in the housing and formed to press the second end of the ampoule toward the first end, and a visible non-linear scale representing the relationship between a volume of medicament delivered from the first end of the ampoule and a distance that the piston has traveled in the housing toward the first end.

2. The apparatus of claim 1, wherein the ampoule includes a travel limit coupled to the body adjacent to the first end.

3. The apparatus of claim 2, wherein the body includes a wall extending between the first and second ends and the wall is formed to fold about the travel limit in the passageway of the housing.

4. The apparatus of claim 2, wherein the travel limit includes tabs that cooperate with housing to couple the ampoule in the passageway of the housing.

5. The apparatus of claim 4, wherein the tabs engage the housing.

6. The apparatus of claim 4, wherein the tabs are spaced-apart from the housing a distance sufficient to permit limited movement between the ampoule and the housing.

7. The apparatus of claim 1, wherein the ampoule includes a rigid plate coupled to the first end.

8. The apparatus of claim 7, wherein the ampoule includes a neck extending through the rigid plate and away from the housing.

9. The apparatus of claim 8, wherein the ampoule includes a travel limit adjacent to the first end and the neck is coupled to the travel limit.

10. The apparatus of claim 1, wherein the housing is transparent.

11. The apparatus of claim 1, wherein the second end of the ampoule is formed to include micropores.

12. The apparatus of claim 1, wherein the ampoule includes a wall extending between first and second ends and the wall includes at least one bellows.

13. The apparatus of claim 12, wherein the at least one bellows is formed to include micropores.

14. The apparatus of claim 1, further comprising a piston-drive system formed to apply a force to piston to dispense medicament from apparatus.

15. The apparatus of claim 14, wherein the piston-drive system includes a torque-production system and an actuator system.

16. The apparatus of claim 14, wherein the piston-drive system includes a cam.

17. A fluid-delivery apparatus for delivering a constant volume of medicament to a patient, the apparatus comprising:

a housing defining a passageway, a bellowed ampoule positioned to lie in the passageway of the housing, the ampoule including first and second and being formed to define a cavity configured to contain the medicament, a piston formed for movement in the housing to press the second end of the ampoule toward the first end, and a piston-drive system cooperating with the piston, the piston-drive system adjusting the movement of the piston in the housing so that the medicament is delivered in uniform increments from the first end of the ampoule.

18. The apparatus of claim 17, wherein the piston-drive system includes a torque-production system and an actuator system.

19. The apparatus of claim 18, wherein the actuator system includes an encoder and a controller in communication with the torque-production system.

20. The apparatus of claim 19, wherein the torque-production system includes a motor in communication with the encoder, a gear train coupled to the motor and in mechanical communication with the piston.

21. The apparatus of claim 17, wherein the piston-drive system includes a cam formed for rotation about a shaft and in mechanical communication with the piston.

22. A fluid-delivery apparatus for delivering a constant volume of medicament to a patient, the apparatus comprising:

a housing defining a passageway, a bellowed ampoule positioned to lie in the passageway of the housing, the ampoule including first and second and being formed to define a cavity configured to contain the medicament, a piston formed for movement in the housing to press the second end of the ampoule toward the first end, and a piston-drive system cooperating with the piston, the piston-drive system adjusting the movement of the piston in the housing so that the medicament is delivered in uniform increments from the first end of the ampoule, wherein the piston-drive system includes a cam formed for rotation about a shaft and in mechanical communication with the piston, and the cam includes a cam surface that changes in radius to dispense successive equal volumes of medicament from the ampoule.

23. The apparatus of claim 22, wherein the cam surface includes a ramp.

24. A method for determining the amount of fluid delivered from a bellowed ampoule positioned in a cylindrical housing having a radius of $r_0$ that is substantially equal to an outermost radius of the ampoule, the method comprising the steps of:

calculating the relative encroachment function Err of the bellowed ampoule from the equation $$\text{Err} = \Psi \cdot (1 - \Psi/3), \text{ where } \Psi = (c/r_0)\sqrt{1-(z/c)^2},$$

z is the height of one half-fold of one bellow of the ampoule, and c is length of an upper panel of one bellow, depressing the ampoule a pre-determined distance in the housing changing the height z of one half-fold of one bellow, and determining the cumulative volume dispensed $V_d$ from the bellowed ampoule from the equation $$V_d = V_0 - (\pi r_0^2 n z) \cdot [1 - \text{Err}],$$

where $V_0$ is the initial volume of the filled reservoir and n is the number of half folds in the bellowed ampoule.

25. A method for delivering a constant linear volume of fluid from a bellowed ampoule positioned in a cylindrical housing having a radius of r that is substantially equal to an outermost radius of the ampoule, the method comprising the steps of:

calculating the relative encroachment function Err of the bellowed ampoule from the equation $$Err = \Psi \cdot (1 - \Psi/3), \text{ where } \Psi \equiv (c/r_0)\sqrt{1-(z/c)^2},$$

z is the height of one half-fold of one bellow of the ampoule, and c is length of an upper panel of one bellow, determining the cumulative volume dispensed $V_d$ from the bellowed ampoule from the equation $$V_d = V_0 - (\pi r_0^2 nz) \cdot [1 - Err],$$

where $V_0$ is the initial volume of the filled reservoir and n is the number of half folds in the bellowed ampoule, and compressing the ampoule in the housing at a rate sufficient to achieve a constant linear flow of fluid from the ampoule in accordance with the equation $$dz/dV_d = \left(-\pi n \cdot \left[r_0^2 \cdot [1 - Err] + \left(\frac{1 + 2\psi/3}{\psi}\right) \cdot z^2\right]\right)^{-1}.$$

* * * * *